(12) United States Patent
Hall

(10) Patent No.: US 9,737,392 B2
(45) Date of Patent: Aug. 22, 2017

(54) IMPLANT, AND METHOD AND SYSTEM FOR PRODUCING SUCH AN IMPLANT

(71) Applicant: Nobel Biocare Services AG, Glattbrugg (CH)

(72) Inventor: Jan Hall, Gothenburg (SE)

(73) Assignee: Nobel Biocare Services AG, Kloten (CH)

( * ) Notice: Subject to any disclaimer, the term of this patent is extended or adjusted under 35 U.S.C. 154(b) by 237 days.

(21) Appl. No.: 14/454,455

(22) Filed: Aug. 7, 2014

(65) Prior Publication Data

US 2015/0026942 A1   Jan. 29, 2015

Related U.S. Application Data

(63) Continuation of application No. 10/499,263, filed as application No. PCT/SE02/02362 on Dec. 18, 2002, now Pat. No. 8,827,703.

(30) Foreign Application Priority Data

Dec. 21, 2001 (SE) .................................... 0104347-0

(51) Int. Cl.
*A61C 13/00* (2006.01)
*A61F 2/00* (2006.01)
(Continued)

(52) U.S. Cl.
CPC .......... *A61F 2/0077* (2013.01); *A61B 17/866* (2013.01); *A61C 8/0018* (2013.01);
(Continued)

(58) Field of Classification Search
CPC ............ A61C 13/0003; A61C 13/0007; A61C 13/001; A61C 13/0012; A61C 13/0018; A61C 13/0019; A61C 13/0004
See application file for complete search history.

(56) References Cited

U.S. PATENT DOCUMENTS 1,698,951 A   1/1929 Holmes
2,215,770 A   9/1940 Sheffield
(Continued)

FOREIGN PATENT DOCUMENTS

DE   413 0 891   3/1992
DE   199 31 701   1/2001
(Continued)

OTHER PUBLICATIONS

Nov. 3, 2004 International Search Report, Application No. PCT/SE 2003/001973, 3 pages.
(Continued)

*Primary Examiner* — Julianna N Harvey
(74) *Attorney, Agent, or Firm* — Knobbe Martens Olson & Bear LLP

(57) ABSTRACT

In a method and system for producing an implant, the latter is designed with one or more surfaces extending in the longitudinal direction of the implant. Two or three production stages can be used. In one stage, either a topography with a long wave pattern is produced by means of cutting work, or laser bombardment or further cutting work is used to produce a topography with an intermediate-length wave pattern. In addition, an oxidation process or shot-peening or etching is used to produce an outer layer. When using two of said production stages, said cutting work or said laser bombardment or further cutting work is followed by the oxidation process or the shot-peening or etching method. When using all three production stages, cutting work is followed by laser bombardment, or further cutting work, which in turn is followed for example by the oxidation process. The invention also relates to an implant which is produced using the method and is identified, ordered and produced using the system. The invention permits effective treatment of different implant situations.

5 Claims, 4 Drawing Sheets

Figure 5:
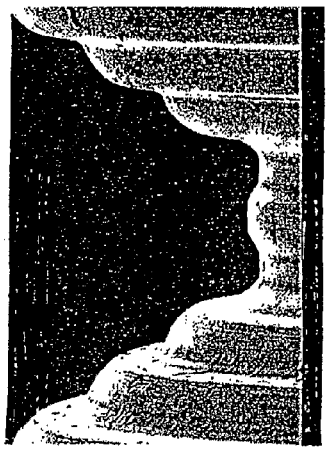

(51) Int. Cl.
  *A61B 17/86* (2006.01)
  *A61C 8/00* (2006.01)
  *A61L 27/30* (2006.01)
  *A61F 2/28* (2006.01)
  *A61F 2/30* (2006.01)

(52) U.S. Cl.
  CPC ........ *A61F 2/2803* (2013.01); *A61F 2/30771* (2013.01); *A61F 2/30942* (2013.01); *A61L 27/30* (2013.01); *A61C 2008/0046* (2013.01); *A61F 2/3094* (2013.01); *A61F 2/30767* (2013.01); *A61F 2002/2817* (2013.01); *A61F 2002/30004* (2013.01); *A61F 2002/3085* (2013.01); *A61F 2002/3097* (2013.01); *A61F 2002/30322* (2013.01); *A61F 2002/30866* (2013.01); *A61F 2002/30924* (2013.01); *A61F 2002/30925* (2013.01); *A61F 2002/30953* (2013.01); *A61F 2240/002* (2013.01); *A61F 2250/0014* (2013.01); *A61F 2250/0026* (2013.01); *A61F 2310/00598* (2013.01); *A61F 2310/00616* (2013.01); *Y10T 29/5191* (2015.01)

(56) References Cited

U.S. PATENT DOCUMENTS

| | | |
|---|---|---|
| 3,672,058 A | 6/1972 | Nikoghossian |
| 3,797,113 A | 3/1974 | Brainin |
| 3,849,887 A | 11/1974 | Brainin |
| 4,103,422 A | 8/1978 | Weiss et al. |
| 4,406,623 A | 9/1983 | Grafelmann et al. |
| 4,431,416 A | 2/1984 | Niznick |
| 4,468,200 A | 8/1984 | Munch |
| 4,547,157 A | 10/1985 | Driskell |
| 4,645,453 A | 2/1987 | Niznick |
| 4,713,003 A | 12/1987 | Symington et al. |
| 4,723,913 A | 2/1988 | Bergman |
| 4,738,623 A | 4/1988 | Driskell |
| 4,758,161 A | 7/1988 | Niznick |
| 4,826,434 A | 5/1989 | Krueger |
| 4,863,383 A | 9/1989 | Grafelmann |
| 4,932,868 A | 6/1990 | Linkow et al. |
| 4,960,381 A | 10/1990 | Niznick |
| 4,976,739 A | 12/1990 | Duthie |
| 5,000,686 A | 3/1991 | Lazzara et al. |
| 5,007,835 A | 4/1991 | Valen |
| 5,061,181 A | 10/1991 | Niznick |
| 5,062,800 A | 11/1991 | Niznick |
| 5,071,350 A | 12/1991 | Niznick |
| 5,074,790 A | 12/1991 | Bauer |
| 5,076,788 A | 12/1991 | Niznick |
| RE33,796 E | 1/1992 | Niznick |
| 5,078,607 A | 1/1992 | Niznick |
| 5,087,201 A | 2/1992 | Mondani et al. |
| 5,150,304 A * | 9/1992 | Berchem ............ A61F 2/30942 623/901 |
| 5,195,892 A | 3/1993 | Gersberg |
| 5,226,766 A | 7/1993 | Lasner |
| 5,230,590 A | 7/1993 | Bohannan et al. |
| 5,328,371 A | 7/1994 | Hund et al. |
| 5,343,391 A | 8/1994 | Mushabac |
| 5,427,527 A | 6/1995 | Niznick et al. |
| 5,433,606 A | 7/1995 | Niznick |
| 5,435,723 A | 7/1995 | O'Brien |
| 5,439,381 A | 8/1995 | Cohen |
| 5,484,286 A | 1/1996 | Hansson |
| 5,527,183 A | 6/1996 | O'Brien |
| 5,571,017 A | 11/1996 | Niznick |
| 5,580,246 A | 12/1996 | Fried et al. |
| 5,584,629 A | 12/1996 | Bailey et al. |
| 5,588,838 A | 12/1996 | Hansson et al. |
| 5,601,429 A | 2/1997 | Blacklock |
| 5,628,630 A | 5/1997 | Misch et al. |
| 5,639,237 A | 6/1997 | Fontenot |
| 5,642,996 A | 7/1997 | Mochida et al. |
| 5,674,072 A | 10/1997 | Moser et al. |
| 5,702,445 A | 12/1997 | Branemark |
| 5,725,375 A | 3/1998 | Rogers |
| 5,759,034 A | 6/1998 | Daftary |
| 5,782,918 A | 7/1998 | Klardie et al. |
| 5,795,160 A | 8/1998 | Hahn et al. |
| 5,810,590 A | 9/1998 | Fried et al. |
| 5,816,812 A | 10/1998 | Kownacki et al. |
| 5,820,374 A | 10/1998 | Simmons et al. |
| 5,823,776 A | 10/1998 | Duerr et al. |
| 5,823,777 A | 10/1998 | Misch et al. |
| 5,871,356 A | 2/1999 | Guedj |
| 5,876,453 A | 3/1999 | Beaty |
| 5,897,319 A | 4/1999 | Wagner et al. |
| 5,915,968 A | 6/1999 | Kirsch et al. |
| 5,938,444 A | 8/1999 | Hansson et al. |
| 5,967,783 A | 10/1999 | Ura |
| 6,095,817 A | 8/2000 | Wagner et al. |
| 6,116,904 A | 9/2000 | Kirsch et al. |
| 6,129,730 A | 10/2000 | Bono et al. |
| 6,135,772 A | 10/2000 | Jones |
| 6,149,432 A | 11/2000 | Shaw et al. |
| 6,200,345 B1 | 3/2001 | Morgan |
| 6,227,859 B1 | 5/2001 | Sutter |
| 6,273,722 B1 | 8/2001 | Phillips |
| 6,283,754 B1 | 9/2001 | Wöhrle |
| 6,287,117 B1 | 9/2001 | Niznick |
| 6,312,259 B1 | 11/2001 | Kvarnstrom et al. |
| 6,315,564 B1 | 11/2001 | Levisman |
| 6,364,663 B1 | 4/2002 | Dinkelacker |
| 6,394,806 B1 | 5/2002 | Kumar |
| 6,402,515 B1 | 6/2002 | Palti et al. |
| 6,419,491 B1 | 7/2002 | Ricci et al. |
| 6,481,760 B1 | 11/2002 | Noel et al. |
| 6,626,671 B2 | 9/2003 | Klardie et al. |
| 6,655,961 B2 | 12/2003 | Cottrell |
| 6,655,962 B1 | 12/2003 | Kennard |
| 6,679,701 B1 | 1/2004 | Blacklock |
| 6,726,689 B2 | 4/2004 | Jackson |
| 6,733,291 B1 | 5/2004 | Hurson |
| 6,733,503 B2 | 5/2004 | Layrolle et al. |
| 6,769,913 B2 | 8/2004 | Hurson |
| 6,913,465 B2 | 7/2005 | Howlett et al. |
| 6,955,258 B2 | 10/2005 | Howlett et al. |
| 7,014,464 B2 | 3/2006 | Niznick |
| 7,108,510 B2 | 9/2006 | Niznick |
| 7,249,949 B2 | 7/2007 | Carter |
| 7,273,373 B2 | 9/2007 | Horiuchi |
| 7,281,925 B2 | 10/2007 | Hall |
| 7,383,163 B2 | 6/2008 | Holberg |
| 8,016,594 B2 | 9/2011 | Ferris et al. |
| 2002/0102518 A1 | 8/2002 | Mena |
| 2002/0106612 A1 | 8/2002 | Back et al. |
| 2002/0177106 A1 | 11/2002 | May et al. |
| 2004/0049201 A1 | 3/2004 | Dinkelacker |
| 2004/0121286 A1 | 6/2004 | Aravena et al. |
| 2005/0147942 A1 | 7/2005 | Hall |
| 2005/0214714 A1 | 9/2005 | Wohrle |
| 2005/0260540 A1 | 11/2005 | Hall |
| 2005/0287497 A1 | 12/2005 | Carter |
| 2006/0172257 A1 | 8/2006 | Niznick |
| 2006/0183078 A1 | 8/2006 | Niznick |
| 2007/0099153 A1 | 5/2007 | Fromovich |
| 2008/0014556 A1 | 1/2008 | Neumeyer |
| 2008/0032264 A1 | 2/2008 | Hall |
| 2008/0261175 A1 | 10/2008 | Hurson |
| 2008/0261176 A1 | 10/2008 | Hurson |
| 2009/0081612 A1 | 3/2009 | Jorneus |
| 2009/0305192 A1 | 12/2009 | Hall |

FOREIGN PATENT DOCUMENTS

| | | |
|---|---|---|
| DE | 102 31 743 | 2/2004 |
| EP | 0 475 358 | 3/1992 |
| EP | 0 676 179 | 10/1995 |
| EP | 0 707 835 | 4/1996 |
| EP | 1 396 236 | 3/2004 |

(56) References Cited

FOREIGN PATENT DOCUMENTS

| | | |
|---|---|---|
| EP | 1 609 436 | 12/2005 |
| EP | 1 728 486 | 12/2006 |
| FR | 2600246 | 12/1987 |
| FR | 2610512 | 8/1988 |
| JP | 11-502454 | 3/1993 |
| JP | 8-501962 | 3/1996 |
| JP | 3026125 | 4/1996 |
| JP | 10-052445 | 2/1998 |
| JP | 2000-504607 | 4/2000 |
| WO | WO 94/07428 | 4/1994 |
| WO | WO 94/09717 | 5/1994 |
| WO | WO 95/09583 | 4/1995 |
| WO | WO 95/12369 | 5/1995 |
| WO | WO 96/16611 | 6/1996 |
| WO | WO 97/05238 | 2/1997 |
| WO | WO 99/23971 | 5/1999 |
| WO | WO 00/00103 | 1/2000 |
| WO | WO 00/03657 | 1/2000 |
| WO | WO 00/62831 | 10/2000 |
| WO | WO 00/72775 | 12/2000 |
| WO | WO 00/72777 | 12/2000 |
| WO | WO 01/49199 | 7/2001 |
| WO | WO 01/74412 | 10/2001 |
| WO | WO 01/76653 | 10/2001 |
| WO | WO 03/013383 | 2/2003 |
| WO | WO 03/015654 | 2/2003 |
| WO | WO 03/030767 | 4/2003 |
| WO | WO 03/034951 | 5/2003 |
| WO | WO 03/055405 | 7/2003 |
| WO | WO 03/055406 | 7/2003 |
| WO | WO 03/059189 | 7/2003 |
| WO | WO 03/061510 | 7/2003 |
| WO | WO 03/063085 | 7/2003 |
| WO | WO 2004/098442 | 11/2004 |
| WO | WO 2004/103202 | 12/2004 |
| WO | WO 2005/117742 | 12/2005 |

OTHER PUBLICATIONS 3.8D series Threaded Implant, dental implant sold before Sep. 27, 1999, Nobel Biocare.

English translation of WO 2005/117742 to Neumeyer, Dec. 15, 2005.

International Preliminary Report on Patentability dated Nov. 25, 2005 for PCT Application No. PCT/IL2004/000438 filed May 23, 2004. Publication No. WO 04/103202 A1 published Dec. 2, 2004.

International Search Report dated Sep. 28, 2004, for Application No. EP04734484 filed May 23, 2004. Publication No. EP 1624826 A1, published Feb. 15, 2006.

Niznick, Gerald A., DMD, MSD. "Proactive Nobel Active New Presentation," Implant Direct™, Oct. 16, 2007.

Supplementary European Search Report dated May 3, 2007, for Application No. EP04734484 filed May 23, 2004. Publication No. EP 1624826 A4, published May 30, 2007.

Board of decision in U.S. Appl. No. 10/583,817, filed Dec. 8, 2008, mailed on Nov. 15, 2013.

Apr. 19, 2007 European Supplementary Search Report for Application No. EP0473448 filed May 23, 2004.

* cited by examiner

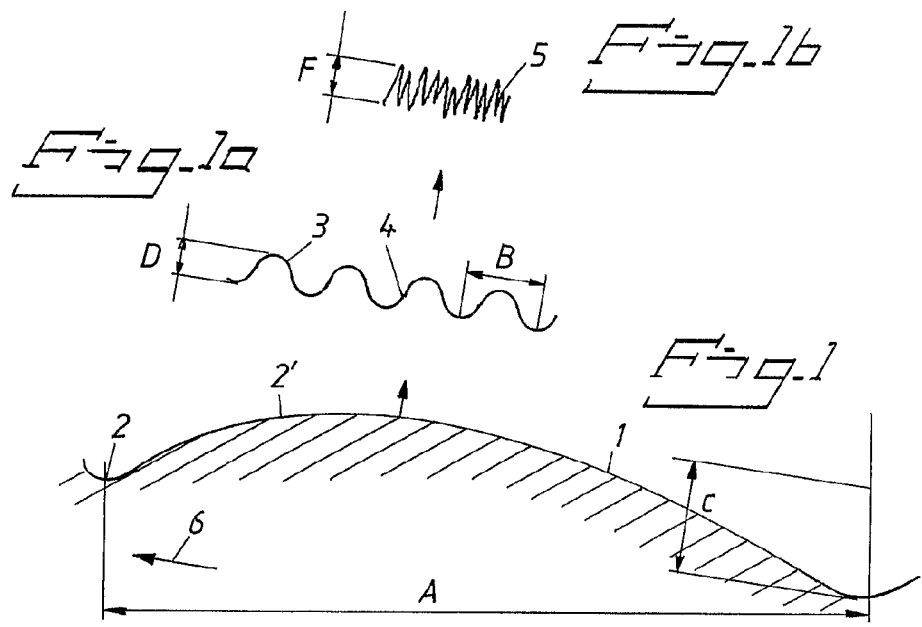
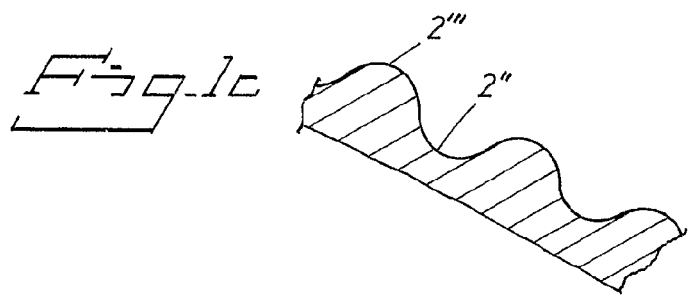
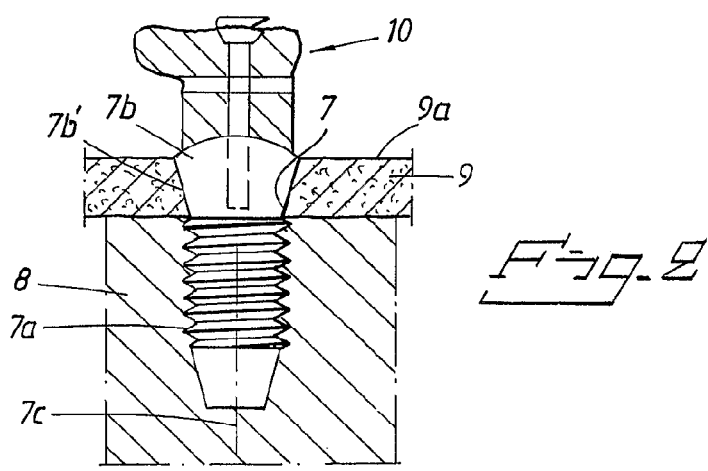

Fig. 7
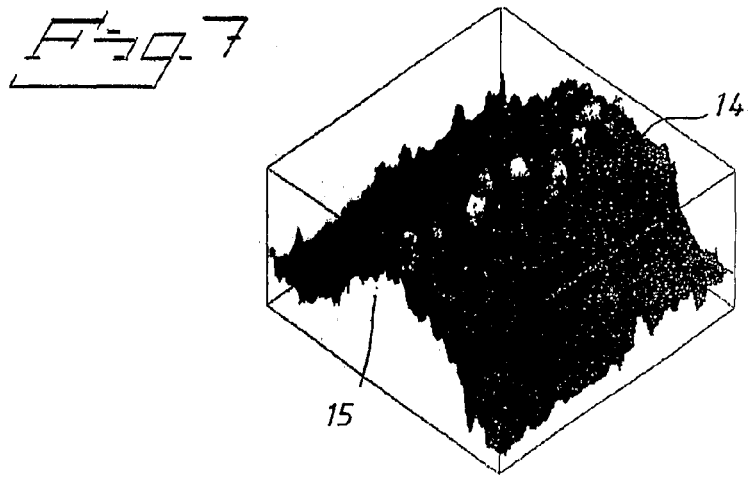
Fig. 8
**Double Wave Topography Combination:
Long & Short Waveform**
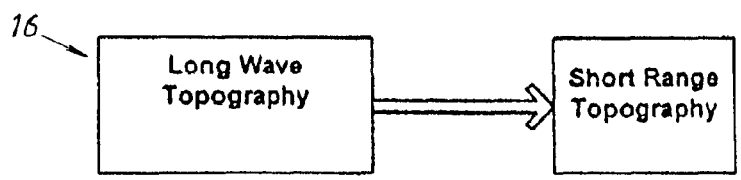
**Double Wave Topography Combination:
Intermediate & Short Waveform**
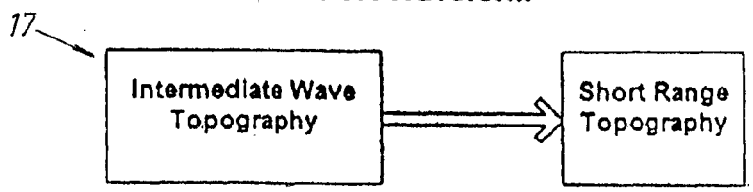
**Triple Wave Topography
Combination**
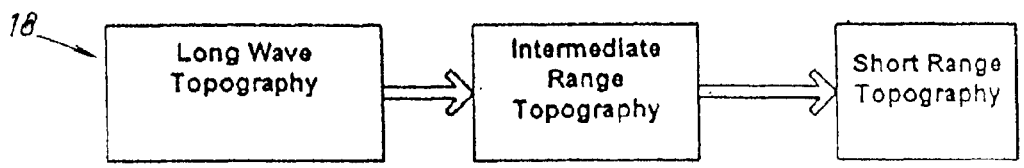

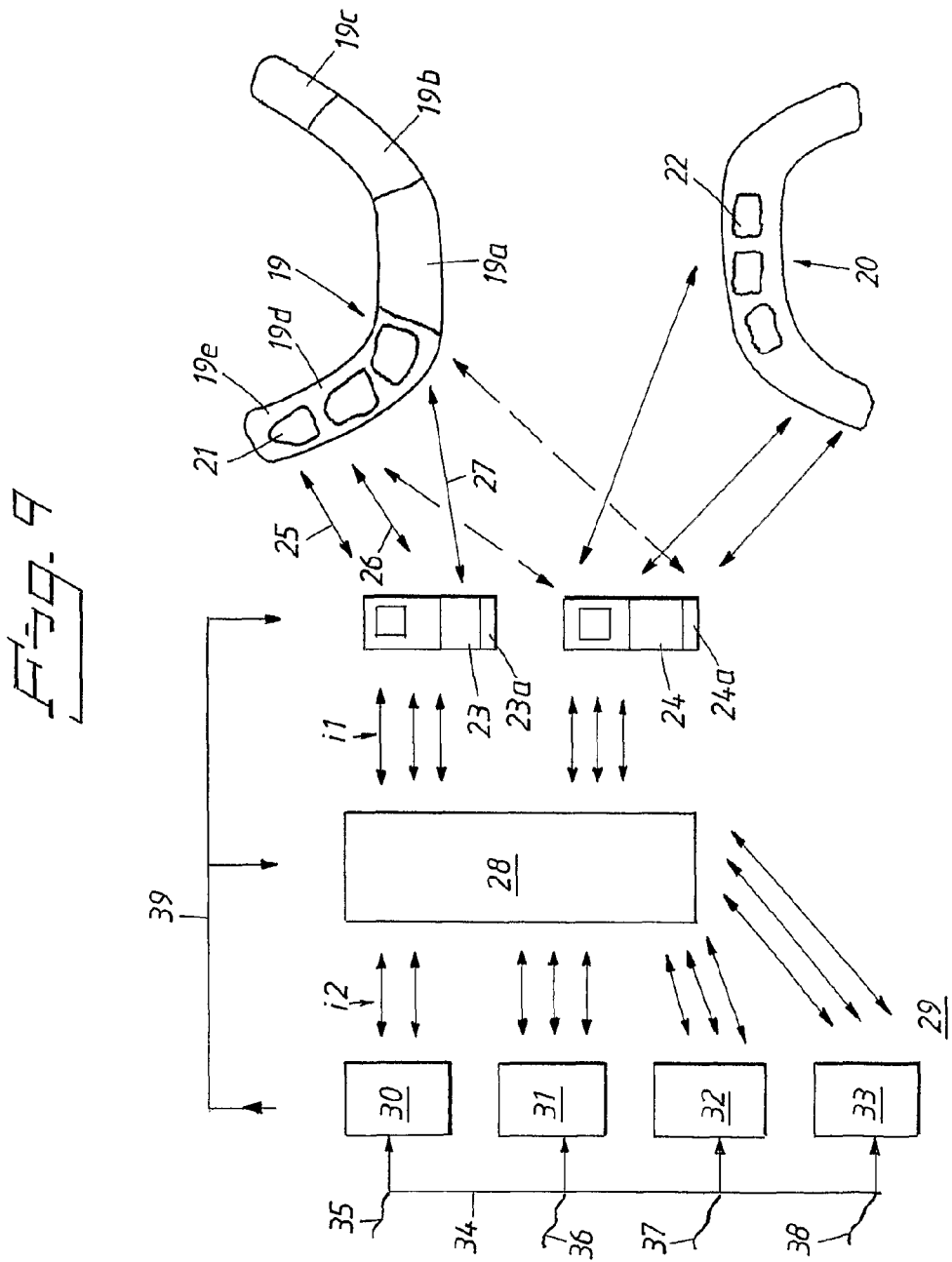

IMPLANT, AND METHOD AND SYSTEM FOR PRODUCING SUCH AN IMPLANT

PRIORITY APPLICATIONS

The present application is a continuation of U.S. patent application Ser. No. 10/499,263, filed May 23, 2005, which is a U.S. National Phase of International Application No. PCT/SE02/02362, filed Dec. 18, 2002, which claims the benefit of Swedish Application No. 0104347-0, filed Dec. 21, 2001. International Application No. PCT/SE02/02362, filed Dec. 18, 2002 being hereby incorporated by reference herein in its entirety.

The present invention relates to a method for producing an implant or fixture which is designed with one or more outer surfaces extending about the longitudinal direction of the implant or fixture. The invention further relates to an implant with such outer surfaces, and to a system for providing the implant. Said system comprises first members for identification and possible analysis and/or modification of the respective implant, second members for transmitting data information related to the identification and possibly to the analysis and/or modification, and third members which, as a function of said data information, are arranged to produce the respective implant.

The present invention is based, inter alia, on the awareness that porous oxide layers on, for example, titanium material can be used to stimulate bone growth when an implant is fitted in bone. A very great many proposals have been made for oxide layer structures, and reference may be made, inter alia, to the patents obtained by the Applicant of the present patent application and to the patent applications made by it: SE 97 01872-5, SE 99 01971-3, SE 99 01974-7, SE 00 01201-3 and SE 00 012002-1. Reference is also made quite generally to U.S. Pat. No. 4,330,891 and EP 676179.

A number of known oxide layer structures have been proposed to function only in cooperation with bone or soft tissue and a number of known oxide layer constructions have been proposed to function as carriers of substances which stimulate bone growth. Reference may be made to the abovementioned patents and patent applications and to the patents obtained by the same Applicant and the patent applications filed: SE 99 01972-1, SE 99 01973-9, SE 01 02388-6, SE 01 02389-4, SE 01 02390-2, SE 01 02391-0 and SE 97 01647-1. Reference may also be made to the patents, patent applications and publications mentioned in said patents and patent applications.

Production of microfabricated outer surfaces on implants has also been discussed in SE 98 01188-5 (from the same Applicant as the present application), U.S. Pat. No. 5,588,838, EP 720454 and EP 475358.

In connection with the fitting of implants, there is a considerable requirement to be able to achieve optimum and high-quality implant results. There is a need to have access to a large number of parameters which can be exploited in different patients and different implantation situations. Given the demands of patients and treatment personnel, not all parameters can be applied in different cases. The bone quality, the attitude of the patients, costs, etc., can be limiting factors, and even if development work and proposals permitting good results are moving in one direction, there may be a need for alternative solutions to be offered or used in different individual cases. Thus, for example, there may be a need to avoid bone-growth-stimulating substances but still use the associated oxide layers together with specific underlying layers. The present invention aims, inter alia, to solve this problem and proposes a novel solution for optimum and effective implant fitments representing specific choices and unique combinations taken from a very wide-ranging assortment of components and designs available on the general market.

The present invention is based on the idea of achieving effective incorporation of an implant in the particular bone, for example the jaw bone, and of thereby achieving substantial stability of the implant in the bone in a short time, for example after just 1 to 5 days. The invention solves this problem too. In one embodiment, it is important to prevent or counteract bacterial growth at the parts where the implant emerges from the bone, for example the jaw bone. This problem too is solved by the invention.

There is also a need to find a technically economical way of obtaining an economical and efficient production chain in which computerized equipment and mechanical production equipment can be used to identify the individual requirement, execute order functions, and produce the identified and ordered implants with a very high degree of precision. The invention solves this problem too.

The feature which can principally be regarded as characterizing a method or an implant according to the invention is that a number of production stages are used for each outer surface concerned. It is thus proposed, inter alia, to produce, by cutting work, a topography with a long wave pattern in which the waves extend substantially in the longitudinal direction of the implant. Alternatively, or in addition, a topography with an intermediate-length wave pattern, in which the waves extend substantially in said longitudinal direction, is to be produced by laser bombardment or cutting work, which can include or use oscillation movements. An oxidation process is also to be used to produce an oxide layer. Alternatively, a shot-peening or etching method can be used to produce a shot-peened or etched layer. According to the invention, at least two of said production stages are used, either said cutting work or said laser bombardment or cutting work to be followed by the oxidation process or shot-peening or etching method. In the case where all three production stages are used, the cutting work is first done, followed by the laser bombardment or the further cutting work, which in turn is followed by the oxidation process, or shot-peening or etching method.

An implant or a fixture according to the present invention can be regarded as being characterized by either of two construction possibilities. In the first case, an underlying wave pattern with long waves or intermediate-length waves is arranged on the surface or its material, and an oxide layer or shot-peened layer or etched layer is arranged on top of the underlying wave pattern. The long waves and intermediate-length waves extend substantially in said longitudinal direction. In the second case, an underlying wave pattern with long waves is used, which in turn is arranged with a wave pattern with intermediate-length waves. An oxide layer or shot-peened or etched layer is arranged on top of the last-mentioned wave pattern. Said long waves and intermediate-length waves extend substantially in said longitudinal direction.

Each wave pattern and layer combination is preferably arranged to obtain values or data for one or more parameters, for example surface area, surface volume and Ra and PV values, which pertain to the actual implant situation. With an optimum increase in surface area and/or an optimum increase in surface volume, each surface is designed with an underlying wave pattern established by cutting work, an intermediate pattern established by laser bombardment or further cutting work, and a top layer established by an oxidation process or by shot-peening or etching. In the case of an underlying wave pattern obtained by cutting work, this pattern comprises substantially parallel troughs or depressions chosen with a depth in the range of 25 to 200 µm, preferably 50 to 150 µm. In the case of a threaded surface or threaded surfaces, for example, the troughs follow each thread spiral in the main direction of the implant. Underlying and intermediate wave patterns which are established by laser bombardment or further cutting work correspondingly comprise substantially parallel troughs or depressions, which can assume depths in the range of 10 to 75 µm and diameters of 75 to 150 µm. The top pattern can be arranged in a manner known per se. Each outer surface can be designed with different wave pattern and layer combinations along its longitudinal extent. At the part of the implant emerging from the bone in question, for example the jaw bone, there is a wave pattern and layer combination which gives a relatively small increase in surface area or surface volume compared to surfaces with said wave pattern and layer combination or wave pattern and layer combinations.

The feature which can principally be regarded as characterizing a system according to the invention is that the data information mentioned in the introduction is designed to initiate or activate wave pattern and layer combinations arranged on top of one another on one or more implant outer surfaces extending in the longitudinal direction of the implant. The computer information can be designed to initiate a first wave pattern and layer combination which comprises, on the one hand, an underlying wave pattern with long waves by means of cutting work or an underlying wave pattern with intermediate-length waves by means of laser bombardment or further cutting work, and, on the other hand, an oxide layer lying on top. In an alternative possibility, the data information can initiate a second wave pattern and layer combination with an underlying wave pattern with long waves by means of cutting work, with a wave pattern lying in between with intermediate-length waves obtained by laser bombardment or cutting work, and a layer lying on top and obtained by an oxidation process, etching or shot-peening.

In one embodiment, the first members mentioned in the introduction are designed to assign different bone parts, for example jaw-bone parts, to different wave pattern and layer combinations. The first members can be arranged to assign hard bone or a hard bone part to wave pattern and layer combinations with only two wave patterns which are arranged one on top of the other and which have a relatively small increase in area and/or volume compared to implants with said wave pattern and layer combinations. The first members can also be arranged to assign medium-hard bone or bone parts to wave pattern or layer combinations with one or two wave patterns arranged on top of one another and layers which give a relatively large increase in area and/or volume compared to the case with implants having wave pattern and layer combinations. The first members can also be arranged to assign soft bone only to wave and layer patterns which have three wave patterns and layers arranged on top of one another, and so on. Further embodiments of the system according to the invention are set out in the dependent claims concerning the system.

By means of what has been proposed above, sophisticated and high-precision treatment methods and implant constructions can be used effectively in the wide variety of existing bone types. Bone formation and healing functions can be effectively stimulated regardless of the bone structure. An advantageous arrangement can be provided for the whole treatment chain involving dentist, dental surgeon, dental technician and the mechanical production.

Figure 6:
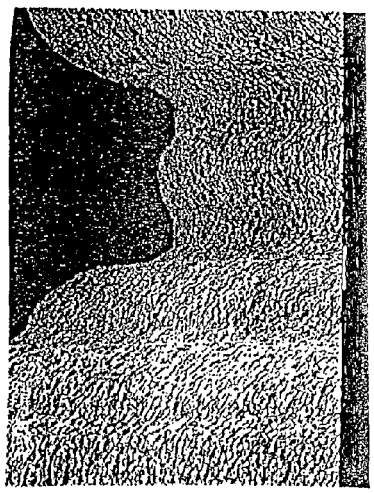
Figure 3:
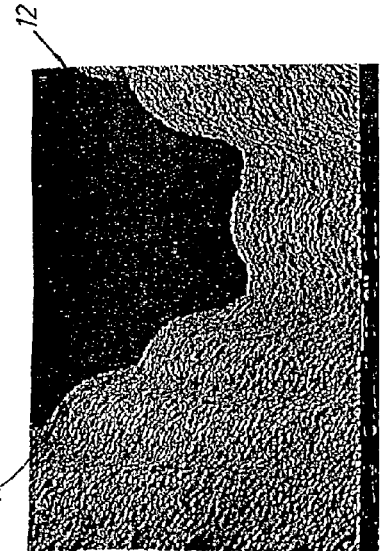
Figure 4:
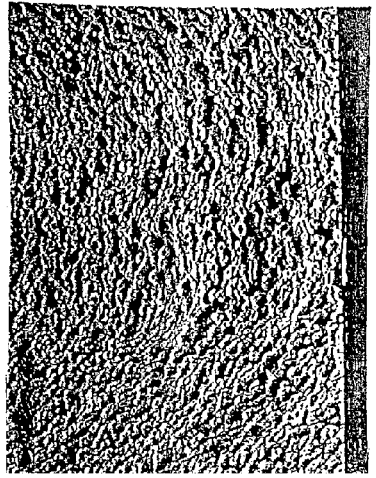

A presently proposed method, implant and system according to the invention will be described below with reference to the attached drawings, in which FIG. 1 shows a diagrammatic representation, on an enlarged scale, of parts of a first underlying wave pattern which has been obtained by means of cutting work, FIG. 1a shows a diagrammatic representation of a second wave pattern, enlarged in relation to FIG. 1 and obtained by laser bombardment, FIG. 1b shows a diagrammatic representation, enlarged in relation to FIGS. 1 and 1a, of a layer which is obtained by means of oxidation, FIG. 1c shows, in longitudinal section, parts of a threaded implant with troughs and peaks, FIG. 2 shows, in vertical cross section, an implant in a partially indicated jaw bone, FIG. 3 shows, in a vertical view, parts of an outer thread of an implant, the outer surface of the thread being designed with underlying troughs covered with an intermediate wave pattern obtained by laser bombardment, and an oxide layer applied on top of the last-mentioned wave pattern, FIG. 4 shows, in a vertical view, and enlarged in relation to FIG. 1, parts of an outer thread of an implant arranged under an intermediate wave pattern established by laser bombardment, and an oxide layer applied on top of said pattern, FIG. 5 shows, in a vertical view, at another scale, a wave pattern with a wave height or wave depth of ca. 75 µm, FIG. 6 shows, in a vertical view, a wave pattern obtained by cutting work and trough depths of 125 µm and outer covering in the form of an oxide layer, FIG. 7 shows, in a perspective view obliquely from outside, a first embodiment of an oxide layer lying on top, FIG. 8 shows, in block diagram form, different wave pattern combinations, FIG. 9 shows a system for assigning wave patterns to different bone parts in the jaw bone and members for identification, transfer and production of implants.

In FIG. 1, an outer part of a thread of an implant is shown by 1. The surface comprises a base structure which is produced in a known manner by cutting work, for example by turning, milling or shot-peening. The base structure is designed with an underlying wave pattern with long waves. The wave length A is chosen in the range of 75 to 250 µm. The outer surface 1 is rippled or undulated with a second wave pattern 3 which has been shown separately and enlarged in FIG. 1a in relation to FIG. 1. The wave length B for the waves or peaks in the second pattern is chosen in the range of 50 to 100 µm, and the waves are joined via troughs or depressions 4. This intermediate layer is obtained by laser application. In the illustrative embodiment according to FIGS. 1, 1a and 1b, the rippled outer surface 3 is in turn provided with an outer layer which consists of an oxide layer 5 shown separately in FIG. 5 and greatly enlarged in relation to FIG. 1b. The trough depth C in the wave pattern 1 can be chosen in the range of 25 to 200 µm, preferably 75 to 150 µm. The wave pattern according to FIG. 1 can be substantially regular or slightly irregular and can be regarded as extending along the main longitudinal direction of the implant, i.e. in a direction parallel to the main direction and indicated by an arrow 6. The course continues along the outer surfaces of the threads, i.e. in a slight zigzag formation along its length. The wave shape can also extend along threaded or unthreaded cone-shaped surfaces.

The wave pattern according to FIG. 1a can have a course substantially corresponding to that of the underlying pattern or can differ from the latter's course. The trough depth D in this pattern can be chosen in the range of 10 to 75 µm.

The oxide layer 5 according to FIG. 1b can be chosen and constructed using a known technique. In one embodiment, the wave pattern 5 can be irregular. The pore depth F can be varied and chosen in the range of 0.01 to 10 µm, preferably 2 to 4 µm.

The invention can be applied to implants 7 in dental situations, for example in connection with the jaw bone 8, which in FIG. 2 has been shown with the trabecular part 8 and the cortical part 9. The implant has one or more outer threads 7a and a part 7b emerging from the upper surface 9b of the jaw bone 9a. A prosthetic structure which can be anchored on the implant is shown symbolically by 10. Different wave pattern combinations can be used on the thread surface(s) and on the outer surface 7b' of the emerging part 7b, the last-mentioned surface preferably being designed with wave patterns giving a slight surface irregularity in order to counteract bacterial accumulation during the process of tissue incorporation. The longitudinal axis of the implant is shown by 7c.

FIG. 3 shows a topography based on a pattern and layer combination, with an underlying wave pattern with long waves 11 having intermediate troughs 12 with depths of about 75 µm. The troughs extend substantially parallel on the threads and follow their pitch in the main longitudinal direction of the implant. The pattern and layer combination has been indicated by 13 and can also include an intermediate wave pattern (see FIGS. 1, 1a and 1b) with intermediate-length waves or short waves obtained by means of laser equipment. An oxide layer lying on top can also be provided.

FIG. 4 is intended to show a pattern combination which is based on intermediate-length waves obtained by laser bombardment and a top oxide layer obtained by an oxidation process.

FIGS. 5 and 6 are intended to illustrate a wave pattern with long waves obtained by machining and with 75 µm trough depth, and a pattern and layer combination with a machined (turned) wave pattern with 125 µm troughs and covered with oxide layer.

The form of an oxide layer 14 has been shown in more detail in FIG. 7. The oxide layer follows the shape of the underlying wave pattern, i.e. the pattern shape which has been shown by 15. A pore and ridge arrangement which is known per se is present on the top face of the layer.

FIG. 8 shows a number of pattern and layer combinations which have different properties. A first pattern combination 16 includes a long wave topography which has been obtained by means of machining and production of troughs of 75 µm in accordance with the above. The long wave topography serves as an underlying wave pattern, on which an oxide layer has been applied with the aid of an oxidation process, which can be of a type known per se, cf. the references mentioned in the introduction.

In a second pattern combination 17, a double wave topography is used which comprises a wave pattern with intermediate-length waves. This wave pattern can be formed in a manner known per se with the aid of laser equipment, by means of which the implant outer surface or thread outer surface in question is bombarded. In this case, on the pattern with intermediate-length waves, an oxide layer is arranged which is applied in a manner known per se using an oxidation process.

A further topography arrangement is shown by 18. In this case, the original surface of the implant or its thread has been produced by cutting work, for example turning, milling or shot-peening, so that a long wave pattern with troughs of 75 µm is formed. A wave pattern lying in between with an intermediate-length topography, which is obtained for example by said laser bombardment, is arranged on the first wave pattern. An oxide layer is in turn arranged on said layer lying in between.

In FIG. 9, an upper jaw is indicated by 19 and a lower jaw by 20. In the figure, teeth have been indicated by 21 and 22, respectively. The jaw bone in question can comprise different parts 19a, 19b, 19c, 19d and 19e. The different parts have different degrees of hardness and, when being provided with implants, they should be treated differently in order in each case to achieve a satisfactory implantation result.

Thus, the hard part 19a requires an implant with a lower Ra value. Bone growth and tissue incorporation is in this case less dependent on, for example, the surface area and surface volume of the implant with surfaces which can cooperate with the bone. The parts 19b and 19d represent medium-hard bone, where other considerations may apply as regards the choice of parameters. The parts 19c and 19e represent soft bone parts where once again it may be important to have implants with a large surface area and large volume against the bone structure in question. According to FIG. 9, computer-based devices 23, 24 are provided by means of which identifications of jaw-bone status, implant type, etc., can be identified and evaluated. The devices 23 and 24 also permit an analysis of the implant situation in question, and possible adjustments or virtual applications can be made in order to comply with the situation in question. Said analysis, adjustments and so on can be carried out based on the experience of the personnel involved. Library functions can also be used and have been symbolized by 23a and 24a. Experiences, standard functions, algorithms, etc., can be stored in said library functions and can be retrieved for said definition, analysis and/or adjustment.

Scanning functions can be provided for the various bone parts, which has been illustrated by arrows 25, 26 and 27. The bone parts and the jaw bone according to FIG. 9 can be related to different patients, and the solid-line and broken-line arrows show that each patient or patient group can use and be served by the different devices 23 and 24, which can be of a type known per se.

FIG. 9 also indicates the case where identified, analyzed and/or adjusted installations or implants, implant types, etc., can be designed to form part of order information i1 which is symbolized by solid arrows. The order can be sent to a central unit which serves a number of dentists or to a central unit 28 which is intended for a specific group of dentists, surgeons, etc. In one embodiment, the transfer of the information i1 can take place via the public telephone and/or computer networks in a manner known per se. The central unit 28 comprises or in turn uses machinery 29 which obtains data information (data files) from the unit 28 or directly from the devices 23, 24, by means of which information the different machine parts can be controlled. The data information i2 is symbolized by solid arrows in the figure. The solid arrows or the communications for the data information or data information items i1, i2 can be two-directional. The machine unit or production unit can comprise or use different types of equipment. Thus, for example, a device 30 which effects cutting work to give a wave pattern with a trough depth of 75 µm can be used. In FIG. 9, a device 31 has been provided to effect cutting work which gives a wave pattern with a trough depth of 125 µm. Laser treatment of outer surfaces is effected in a device 32, and, in a device 33, an oxide layer is obtained on the outer surfaces with the aid of oxidation equipment. The device 32 can alternatively represent cutting work with oscillation movements in a known manner. Alternatively, the device 33 can represent a shot-peening unit, for example a sandblasting unit of known type, or an etching apparatus which uses acid (hydrofluoric acid) and nitric acid in a known manner. An HF mixture consisting of hydrofluoric acid and nitric acid can be used here.

The various devices 30, 31, 32 and 33 can be designed in a manner known per se, and reference is made to the general prior art, see also the references mentioned in the introduction. A blank for producing the implant or fixture is treated in order to obtain the abovementioned pattern combinations, the implant or equivalent being transferred to the various devices 30, 31, 32 and 33 by a link or by transport which has been indicated by 34. The various treatment stages have been symbolized by 35, 36, 37 and 38. The return of the treated or produced implant to the central unit 28 and to the dentist, surgeon, hospital, etc., has been symbolized by 39. The central unit can constitute an intermediate stage which receives orders and ensures production in the machinery 29 and obtains produced or treated implants which are then sent back to the patient treatment site. The direction(s) in which a wave pattern extends can be calculated from a surface start, for example a thread start, and terminate at the surface end or thread end.

The invention is not limited to the illustrative embodiment given above by way of example, and instead it can be modified within the scope of the attached patent claims and the inventive concept. Reference is also made to the Swedish patent application filed on the same day and by the same Applicant and bearing the title "Method for producing a surface structure on an implant, and such an implant".

The invention claimed is:

1. A system for providing an implant or implants for different treatment situations, the system comprising:
   a first member for identification and analysis of a hardness of a bone part;
   a second member for transmitting information related to the identification and analysis of the bone part; and
   a third member that produces an implant with a surface treatment based upon the information related to the identification and analysis of the hardness of the bone part, wherein the third member produces different surface treatments on the implant corresponding to the identification and analysis of the hardness of the bone part.

2. The system of claim 1, wherein the different surface treatments comprise different wave patterns on a dental implant.

3. The system of claim 1, wherein the first member is configured to identify hard, medium and soft bone parts.

4. The system of claim 3, wherein different surface treatments correspond to hard, medium and soft bone parts.

5. The system of claim 4, wherein the different surface treatments comprise different wave patterns on a dental implant.

* * * * *